(12) United States Patent
Van Der Walt (10) Patent No.: US 6,797,913 B2
(45) Date of Patent: Sep. 28, 2004

(54) TREATMENT OF FLUOROCARBON FEEDSTOCKS

(75) Inventor: Izak Jacobus Van Der Walt, Krugersdorp (ZA)

(73) Assignee: South African Nuclear Energy Corporation Limited, Pelindaba (ZA)

( * ) Notice: Subject to any disclaimer, the term of this patent is extended or adjusted under 35 U.S.C. 154(b) by 11 days.

(21) Appl. No.: 10/203,526

(22) PCT Filed: Feb. 9, 2001

(86) PCT No.: PCT/IB01/00158

§ 371 (c)(1), (2), (4) Date: Nov. 19, 2002

(87) PCT Pub. No.: WO01/58584

PCT Pub. Date: Aug. 16, 2001

(65) Prior Publication Data

US 2003/0125473 A1 Jul. 3, 2003

(30) Foreign Application Priority Data

Feb. 10, 2000 (ZA) .......................... 2000/0636

(51) Int. Cl.[7] .............................. B23K 9/02
(52) U.S. Cl. .................. 219/121.41; 204/169
(58) Field of Search ............... 219/121.41, 121.43, 219/121.52, 121.59, 121.44, 121.46, 121.38, 121.31; 204/164, 165, 168–169; 423/507, 258, 257, 488, 489; 422/186.04; 570/150, 142

(56) References Cited

U.S. PATENT DOCUMENTS

| 2,785,119 A | * | 3/1957 | Cook et al. .................. 204/169 |
| 5,026,464 A | | 6/1991 | Mizuno et al. ............. 204/164 |
| 5,611,896 A | * | 3/1997 | Swanepoel et al. ......... 204/169 |
| 5,744,657 A | * | 4/1998 | Webster ....................... 570/150 |
| 5,935,390 A | | 8/1999 | Felix et al. ................. 204/164 |

FOREIGN PATENT DOCUMENTS

EP 0648530 4/1995

* cited by examiner

Primary Examiner—Quang T Van
(74) Attorney, Agent, or Firm—Ladas & Parry (57) ABSTRACT

A method of treating a fluorocarbon feedstock includes radio frequency induction heating of a zone of a reaction chamber to a temperature not exceeding 950° C. The feedstock heats up in the heating zone, and the reaction chamber pressure and heating zone temperature are chosen so that a fluorocarbon compound present in the feedstock dissociates or depolymerizes into a more desired fluorocarbon compound. A hot product gas, which includes the more desired fluorocarbon compound, is formed and then quenched to stabilize the more desired fluorocarbon compound.

12 Claims, 10 Drawing Sheets

TREATMENT OF FLUOROCARBON FEEDSTOCKS

THIS INVENTION relates to the treatment of fluorocarbon feedstocks. It relates in particular to a method of treating a fluorocarbon feedstock.

According to the invention, there is provided a method of treating a fluorocarbon feedstock, which method includes heating, by means of radio frequency induction, a heating zone to a high temperature;

allowing a fluorocarbon feedstock, comprising at least one fluorocarbon compound, to heat up in the heating zone so that the fluorocarbon compound dissociates into at least one fluorocarbon precursor or reactive species; and cooling the fluorocarbon precursor or reactive species, thereby forming, from the fluorocarbon precursor or reactive species, at least one more desired fluorocarbon compound.

The heating zone may thus be provided by a reactor. The reactor may comprise an elongate cylindrical reactor shell providing a reaction chamber which contains the heating zone, and a feedstock holder in the heating zone of the reaction chamber. The reactor shell typically is of quartz, and may have its ends sealed off and water cooled.

The radio frequency induction heating may be provided by a radio frequency induction heating oven having an induction coil within which the heating zone of the reactor is located. In other words, the induction heating coil is located around that part of the reactor shell containing the heating zone.

In one embodiment of the invention, the reactor shell may extend vertically and be stationary. It is believed that this configuration will be particularly suited to treating feedstock in the form of unfilled not directly usable material as hereinafter described.

However, in another embodiment of the invention, the reactor shell may be tilted at an angle to the vertical, eg between about 5° and about 60° to vertical, and it may rotate or vibrate. The reactor may then be provided with a graphite crucible having transverse baffles to regulate the residence time of the feedstock in the reactor. It is believed that this configuration will be particularly suited to treating feedstock in the form of filled material, which is not directly usable as hereinafter described; as the filled material passes downwardly down the reactor, it is depolymerized and evaporates, thus passing upwardly out of the reactor, while filler material passes downwardly out of the bottom of the reactor. Instead, an upright reactor can be used to treat filled material; however, the reactor will then be provided, at its lower end, with a removable plug to drain filler material.

The feedstock may, at least in principle, be in gaseous, liquid or solid particulate form, or in the form of mixtures of two or more of these. When the feedstock is in liquid form, it may be a more-or-less pure feedstock comprising a single fluorocarbon compound, such as $C_6F_{14}$; however, it is envisaged that the feedstock will then normally be a not directly usable fluorocarbon product comprising two or more of a range of fluorocarbon compounds such as $C_5F_{12}$, $C_6F_{14}$ $C_7F_{16}$, $C_8F_{18}$, $C_4F_8$, $C_8F_6$, $(C_3F_7)_3N$, $C_6C_{13}H$, $C_6F_{12}H_2$, or the like. Normally, one compound will be present in such a product as a dominant component, ie constitute the major proportion of such a product. The feedstock may then be fed into the reactor from the bottom.

When the feedstock is in solid particulate form, it may, in particular, be a filled or an unfilled not directly usable material such as polytetrafluoroethylene ('PTFE'), tetrafluoroethylene hexafluoropropylene vinylidenefluoride ('THV'), fluorinated ethylene-propylene copolymer ('FEP'), perfluoroalkoxy copolymer ('PFA'), or the like. By 'filled' is meant that the fluorocarbon feedstock may contain elements or substances such as silica, copper, carbon, etc which were originally added to fluorocarbon material to impart specific properties thereto. Once such material has been used and has thus become, mechanically, not directly usable material, but suitable for use as the feedstock in the method of the invention, it will still contain these filling elements. In the method of the invention, these materials are depolymerized, and the more desirable fluorocarbon compound formed therefrom. The feedstock may then be fed into the reactor from the top or from the bottom.

If desired or necessary, the solid particulate feedstock may be pretreated to remove surface contaminants such as oil and dirt, eg by means of solvent extraction.

Typical products which may be obtained are tetrafluoromethane ($CF_4$), tetrafluoroethylene ($C_2F_4$), hexafluoroethylene ($C_2F_6$), hexafluoropropylene ($C_3F_6$), fluorobutylene ($C_4F_6$), cyclic octafluorobutylene (c-$C_4F_8$), decafluorobutylene ($C_4F_{10}$), octafluoropropylene ($C_3F_8$) and other $C_xF_y$ chains where x and y are integers.

The reactor may operate on a batch, on a semi-continuous, or on a continuous basis. The method will thus include feeding the feedstock into the reactor zone on a batch, on a semi-continuous, or on a continuous basis. By 'batch' is meant that a predetermined quantity of the fluorocarbon is loaded into the reactor and allowed to react to completion with the hot plasma gas. By 'semi-continuous' is meant that a hopper is filled with feedstock, with this feedstock then being fed into the reactor at a continuous, normally constant, feed rate until the hopper is empty, whereafter the hopper may be refilled. By 'continuous' is meant that the feedstock is fed continuously into the reactor, normally at a more-or-less constant feed rate.

While the feedstock may, in principle, be introduced into the cavity or the first zone of the reaction chamber in any desired manner, gravity feed may, in particular, be employed since relatively large feedstock particles can thereby readily be used, eg particles in the size range 1 to 10 mm, preferably 3 to 5 mm. Thus, the feedstock may be fed vertically into the chamber under gravity, immediately above the heating zone.

The cooling of the fluorocarbon species or precursor may be effected in a second zone of the reaction chamber located above the heating or first zone thereof. The cooling may be effected by means of a quench probe, which may be a self-cleaning probe. The self-cleaning quench probe may comprise an outer cylindrical component mounted to the reactor, providing a central passageway and adapted to cool the hot gas passing through the passageway; a plurality of circumferentially spaced elongate teeth or scrapers protruding inwardly from the outer component into the passageway; an inner cylindrical component located with clearance inside the outer component, with the inner component also adapted to cool the hot gas passing along the peripheral gap between the components; a plurality of circumferentially spaced elongate teeth or scrapers protruding outwardly from the inner component into the passageway, with these teeth or scrapers being staggered with respect to the teeth or scrapers on the outer component; and drive means for driving the one cylindrical component to oscillate relative to the other cylindrical component. The drive means may, for example, comprise a spring loaded piston driven arm.

Instead, however, any other suitable quenching means can be used such as rapid expansion of the product gas, gas quenching by means of another gas which is cold, or the like.

The reaction chamber may be operated under pressures ranging from near vacuum to elevated pressures, depending on the more desired fluorocarbon compound required as product and other process variables. Evacuation may be effected through the quench probe.

Normally a spread of fluorocarbon compounds will form as products. The method may then include separating the various products from one another.

According to a second aspect of the invention, there is provided a quench probe which comprises
- an outer cylindrical component providing a central passageway and adapted to cool a hot gas passing through the passageway;
- a plurality of circumferentially spaced elongate teeth or scrapers protruding inwardly from the outer component into the passageway;
- an inner cylindrical component located with clearance inside the outer component, with the inner component adapted to cool the hot gas passing along the peripheral gap between the components;
- a plurality of circumferentially spaced elongate teeth or scrapers protruding outwardly from the inner component into the passageway, with these teeth or scrapers being staggered with respect to the teeth or scrapers on the outer component; and
- drive means for driving the one component to oscillate relative to the other component.

The inner component may be located centrally or concentrically within the outer component. The same number of teeth or scrapers may be provided on the inner and outer components. The teeth or scrapers may be spaced equidistantly apart on their components. The teeth or scrapers may extend parallel to one another.

The components may be hollow and/or may be provided with passages to permit a cooling fluid, such as water, to pass through them in order to cool or quench the hot gas.

The drive means may, as also hereinbefore described, comprise a spring loaded piston driven arm attached to one of the cylindrical components.

Due to the oscillation of the one component relative to the other, cleaning of solidified or sublimated material from the surfaces thereof, on passage of the gas through the annular gap between the components, is achieved.

The quench probe is particularly suited for use in a reactor as hereinbefore described; however, it is not limited only to such use. Normally, the outer component will be fixed to the reactor, with the inner component oscillating relative to the outer component.

The invention will now be described in more detail with reference to the accompanying simplified flow diagrams.

Figure 1:
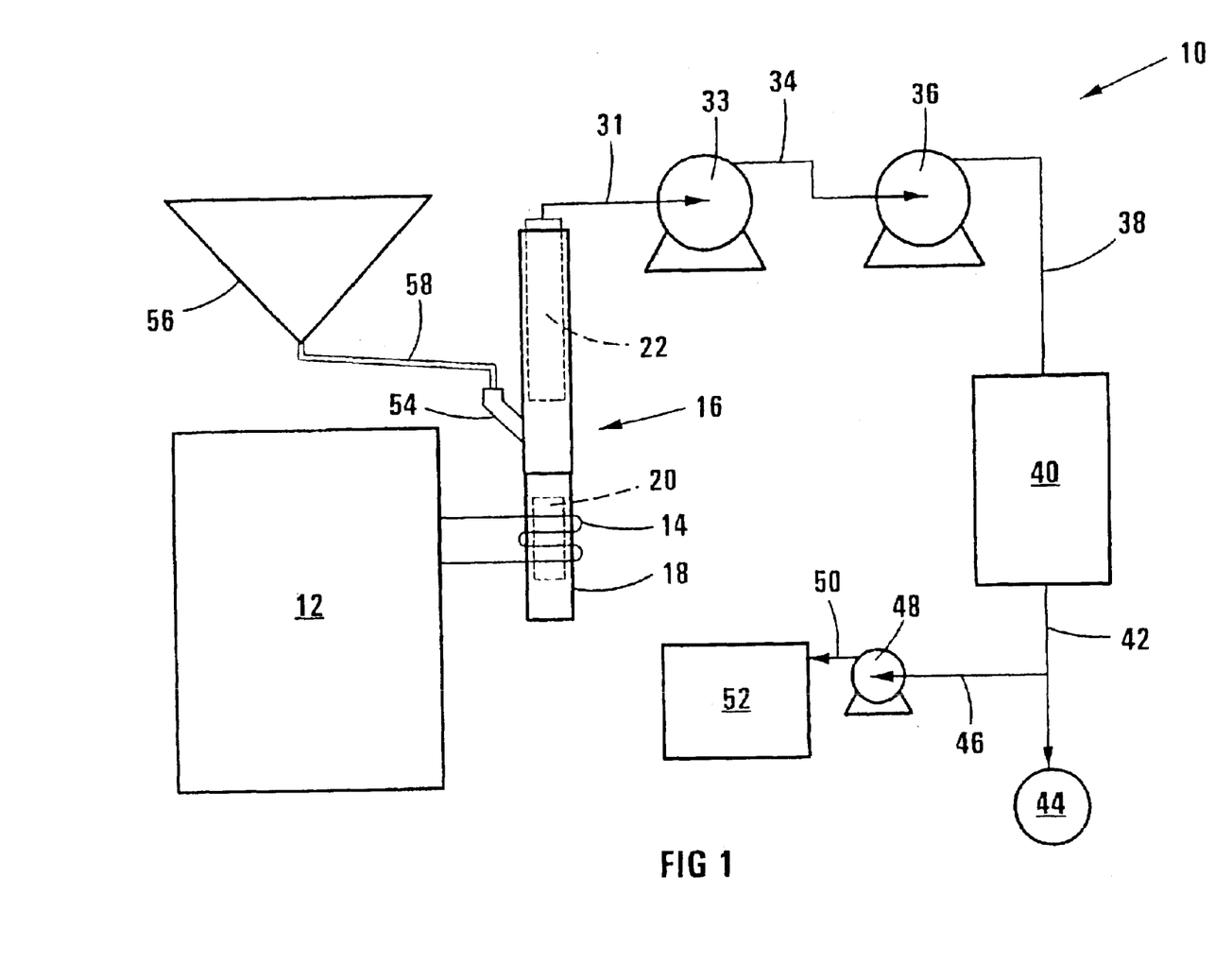
FIG. 1 shows an installation for carrying out a method of treating a fluorocarbon feedstock, according to a first embodiment of the invention.
Figure 2:
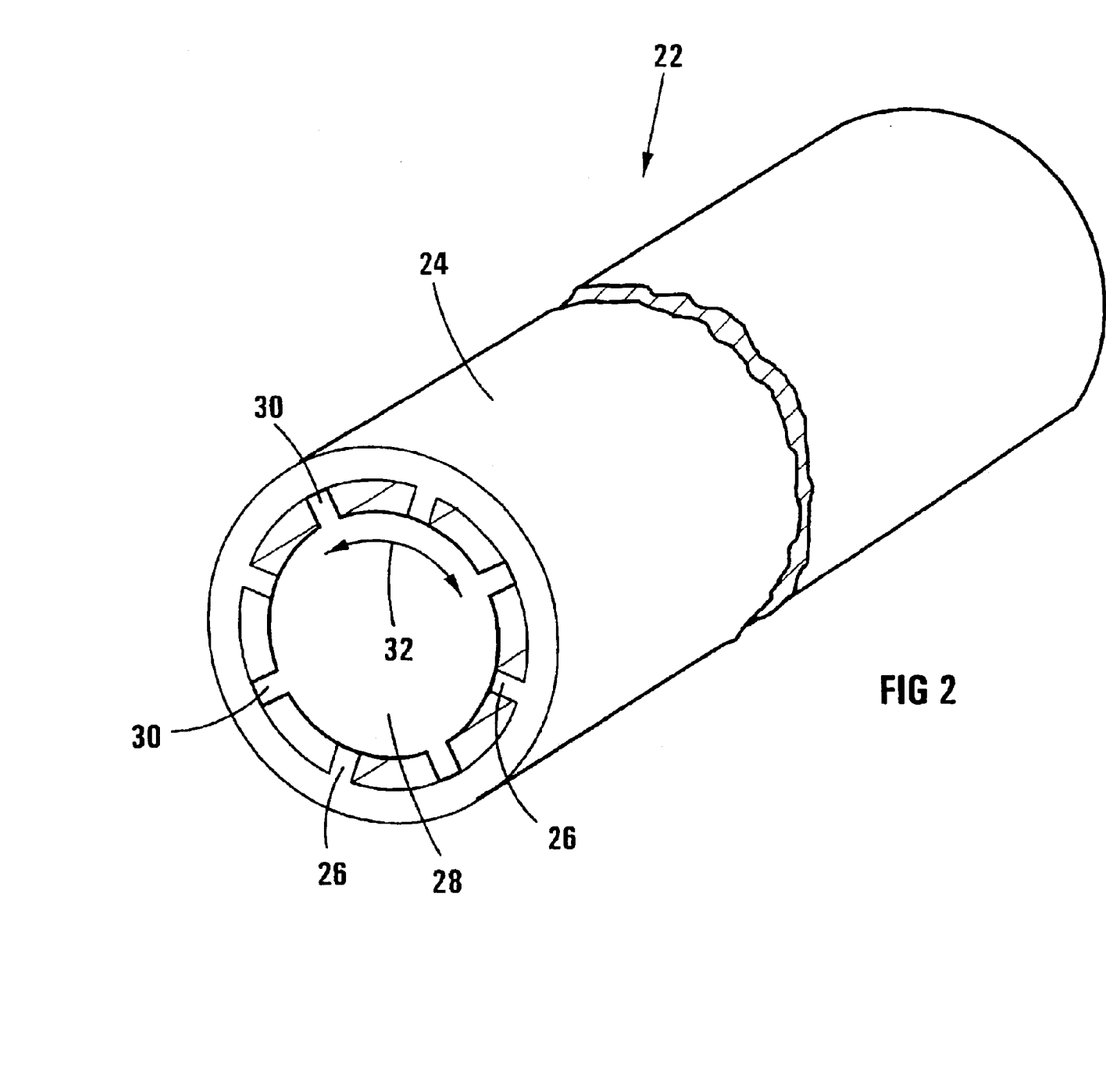
FIG. 2 shows a three-dimensional view of the quench probe of the reactor of FIG. 1.

In FIGS. 1 and 2, reference numeral 10 generally indicates an installation for carrying out a method of treating a fluorocarbon feedstock in accordance with a first embodiment of the invention.

The installation 10 includes a reactor 16. The reactor 16 includes radio frequency power supply (generator) 12 having an induction working coil 14.

The reactor 16 also comprises a stationary quartz shell or tube 18 within which is located a graphite holder or crucible 20. The reactor 16 is thus of elongate form, and is located vertically upwardly.

The lower end of the quartz tube 18 is sealed off and water cooled (not shown), while a self-cleaning quench probe 22 protrudes into its upper end. The self-cleaning quench probe 22 comprises an elongate watercooled cylindrical outer component 24, which is fixed to the reactor 12. The outer component 24 thus has a central passageway into which protrudes equally spaced elongate radially inwardly protruding teeth or scrapers 26. Inside the passageway of the outer component 24 is located, with peripheral clearance, an elongate watercooled cylindrical inner component 28. Equally spaced elongate radially outwardly protruding teeth or scrapers 30 are provided on the inner component 28, with the teeth 30 being spaced circumferentially from the teeth 26. The teeth 26, 30 may extend the full length of the components 24, 28, and the components 24 and 28 are of substantially the same length. The inner component 28 is provided with drive means (not shown), such as a spring loaded piston driven arm, for driving it to oscillate relative to the outer component 24 as indicated by the arrow 32. Removal of solid contaminants from the components 24, 28 is thus achieved by means of the oscillating teeth 26, 30.

The quench probe 22 is thus a double annular water cooled probe designed to cool the gas that forms inside the reactor 16 as hereinafter described, down to below 200° C. at a rate of about $10^{5}$° C./second. The probe is self cleaning to prevent blockages thereof since solidified or sublimated material forms on the surfaces of the probe in use.

A feedstock feed conduit 54 leads into the quartz tube 18 above the crucible 20, with a gravity feeder 56 connected to the conduit 54 by means of a pipe or conduit 58.

An evacuation flow line 31 leads from the upper end of the quench probe 22 to a vacuum pump 33, while a flow line 34 leads from the discharge of the pump 33 to a compressor 36. A flow line 38 leads from the discharge of the compressor 36 to a product storage vessel 40. A withdrawal line 42 leads from the storage vessel 40 to a further processing stage 44 such as a scrubber. A flow line 46 leads from the flow line 42 to a compressor 48, with the discharge of the compressor 48 being connected, by means of a flow line 50, to an analytical system 52.

In use, a high temperature is created in a high temperature zone of the reaction chamber of the reactor 18. By means of the induction coil 14, the crucible 20 located in the high temperature zone is thus heated by means of induction heating. When the required operating temperature has been reached in the heating zone, particulate solid fluorocarbon feedstock is fed into the crucible 20 by means of the feeder 56 and the conduits 58, 54. The heat generated is sufficiently high so that feedstock depolymerization occurs in the crucible 20, with the formation of product gases.

The product gases are immediately quenched by means of the quench probe 22, thereby to form a more desired fluorocarbon compound which is withdrawn along the flow line 31, 34, 38, the vacuum pump 33 and the compressor 36 into the storage vessel 40. The product can be further processed in the processing stage 44, eg to recover a particular, more desired fluorocarbon compound from other less desired products that are formed.

Figure 3:
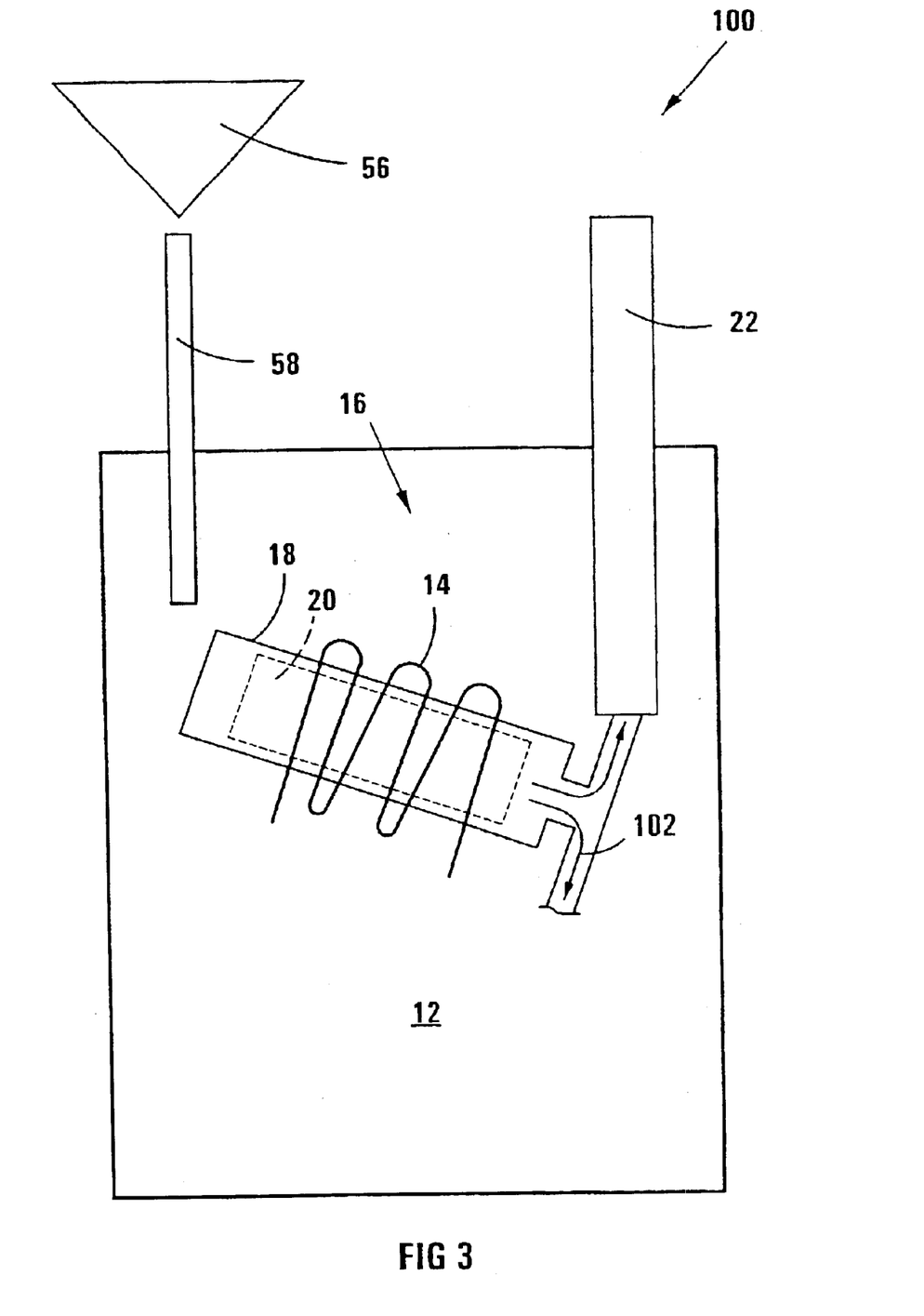
FIG. 3 shows an installation for carrying out a method of treating a fluorocarbon feedstock, according to a second embodiment of the invention.

Referring to FIG. 3, reference numeral 100 generally indicates an installation for carrying out a method of treating a fluorocarbon feedstock, in accordance with a second embodiment of the invention.

Parts of the installation 100 which are the same or similar to those of the installation 10 hereinbefore described, are indicated with the same reference numerals.

In the installation 100, the quartz tube or shell 18 of the reactor 16 is tilted at an angle of between 5° and 60° to the vertical, and is fitted with a graphite crucible 20, having transverse, eg circumferential, internal baffles (not shown). The tube 18 rotates or vibrates. The feedstock enters the upper end of the tube 18 while depolymerized gases, ie product gases, exit from the lower end thereof. Extracted filler material passes out of the bottom of the tube 18, as indicated by arrow 102.

Figure 4:
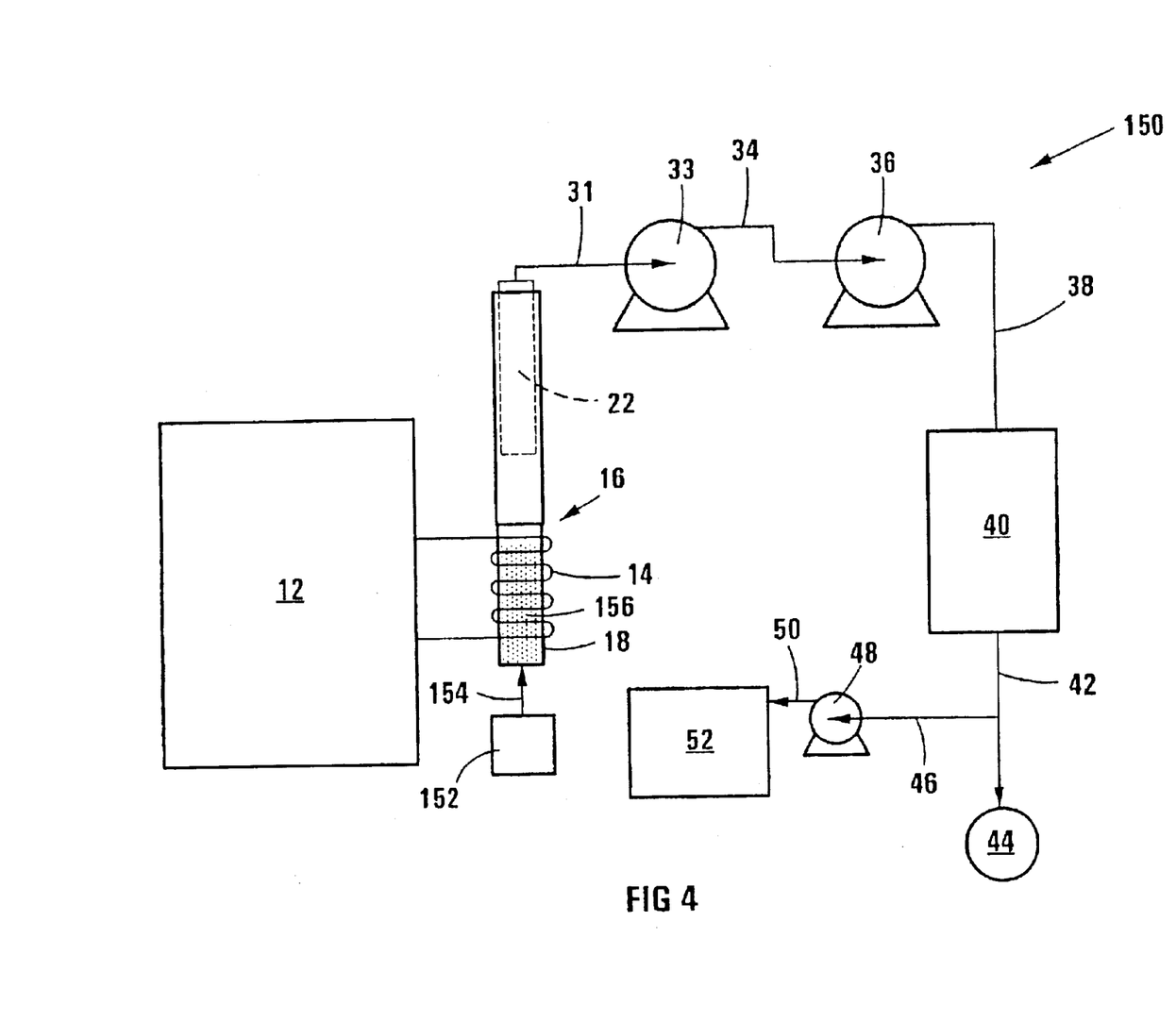
FIG. 4 shows an installation for carrying out a method of treating a fluorocarbon feedstock, according to a third embodiment of the invention.

Referring to FIG. 4, reference numeral 150 generally indicates an installation for carrying out a method of treating a fluorocarbon feedstock, in accordance with a third embodiment of the invention.

Parts of the installation 150 which are the same as or similar to those of the installations 10, 100 hereinbefore described, are indicated with the same reference numerals.

In the installation 150, a liquid feedstock supply 152 is provided. A flaw line 154 leads from the supply 152 into the bottom of the quartz tube 18 of the generator 12 and into a bed 156 of graphite granules.

Thus, in use, the graphite bed 156 is heated by means of the induction coil 14. Liquid feedstock is fed into the bottom of the crucible, passes upwardly through the graphite bed, and is heated and dissociated as hereinbefore described.

Figure 5:
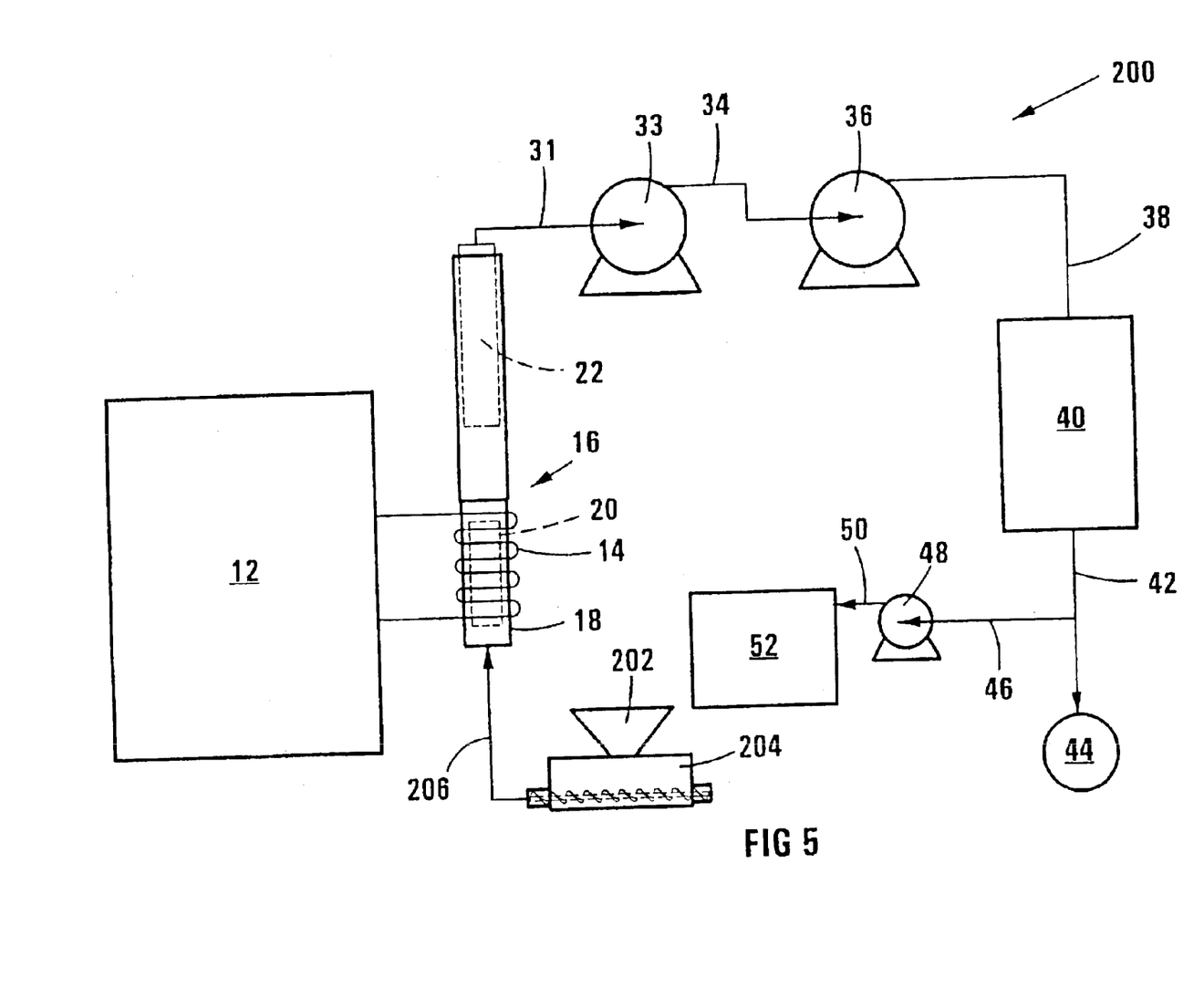
FIG. 5 shows an installation for carrying out a method of treating a fluorocarbon feedstock, according to a fourth embodiment of the invention.

Referring to FIG. 5, reference numeral 200 generally indicates an installation for carrying out a method of treating a fluorocarbon feedstock, in accordance with a fourth embodiment of the invention.

Parts of the installation 200 which are the same as or similar to those of the installations 10, 100 and 150 hereinbefore described, are indicated with the same reference numerals.

The installation 200 includes a hopper 202 for solid particulate feedstock. The hopper 202 is mounted to a screw feeder 204 whose discharge is connected, by means of a conduit 206, to the bottom of the quartz tube 18.

Thus, in use, solid particulate feedstock is fed upwardly from the bottom of the reactor 16. As the solid particulate feedstock is fed in an upwardly direction through the reactor 16 and the graphite crucible 20, it reaches the high temperature heating zone of the reactor, dissociates and is then quenched by the probe 22, as hereinbefore described.

In the Examples, a 10 kW, 800 kHz radio frequency generator operated at 8 kW in accordance with the installation 10 of FIG. 1 was used. The stationary quartz tube 18 of the reactor 16 had a nominal diameter of 70 mm and a length of 300 mm. The system was evacuated through a filter (not shown), by means of a high integrity dry vacuum pump 33. All pressures are indicated in kPa(a) while product yields are recorded as relative volume percent.

EXAMPLE 1

The installation 10 was operated on a continuous basis, with about 2 kg/h of particulate unfilled or spent PTFE material being fed continuously into the crucible 20.

It was found that the reactor 16 needed to be evacuated to a relatively high vacuum in order to yield a maximum amount of TFE. For different product compositions, different feedstock materials and process parameters will be required. Specific pressure and temperature ranges will be characteristic to the product composition required. Thus, to depolymerize PTFE and obtain TFE as the principal product, a reaction temperature of 400° C. to 700° C. and a sub-atmospheric pressure is required in the reactor 16.

It was found that a heating up period of approximately 5 minutes was required to reach the operating temperature of 400° C. to 700° C. During this time, some feedstock was present in the crucible 20, although the feeder was not yet activated. This feedstock softened and began to depolymerize. When the operating temperature had been reached, the feeder 26 was activated to provide the throughput of about 2 kg/h. If desired, the throughput can be varied between 1 kg/h and 10 kg/h feed material for a 10 kW installation.

At an operating temperature of 400° C. to 700° C. and a sub-atmospheric pressure of about 1 kPa immediate depolymerization of the PTFE by means of pyrolysis, took place, with the PTFE being vaporized and broken down into fluorocarbon precursors or reactive species. These precursors or reactive species were immediately quenched by means of the quench-probe 22, to produce TFE. Due to the repolymerization of the TFE gas, accumulation of a finely divided white powder on all the cold surfaces of the reactor 16, was observed. This was subsequently cleaned by the self-cleaning quench probe.

The results obtained are set out in Table 1.

TABLE 1

| Analytical Results | |
|---|---|
| Products | Example 1 - Product gas |
| $CF_4$ (%) | — |
| $C_2F_6$ (%) | 0.062 |
| $C_2F_4$ (%) | 83.9 |
| $C_3F_6$ (%) | 6.83 |
| $c-C_4F_8$ (%) | 9.01 |

PTFE was successfully depolymerized in this example at about 1 kWh/kg PTFE. No major process parameter and hardware scale-up problems are envisaged.

The installation or system 10 was particularly set up to handle not directly usable PTFE material to supplement the production of TFE ($C_2F_4$) which is a precursor for the manufacture of other complex fluorocarbons, eg $c-C_4F_8$. This processing can be performed in the processing stage 44.

Table 1 indicates that surprisingly high yields of $C_2F_4$ were obtained, considering that the configuration of the installation 10 had not been optimized.

EXAMPLE 2

In this example, the conversion of FEP (Fluorinated Ethylene-Propylene copolymer) scrap material into usable high quality products such as TFE (tetrafluoroethylene), HFP (hexafluoropropylene) or $c-C_4F_8$ (cyclic octafluorobutylene) was explored as a function of reactor pressure, for two distinct temperature profiles.

Figure 6:
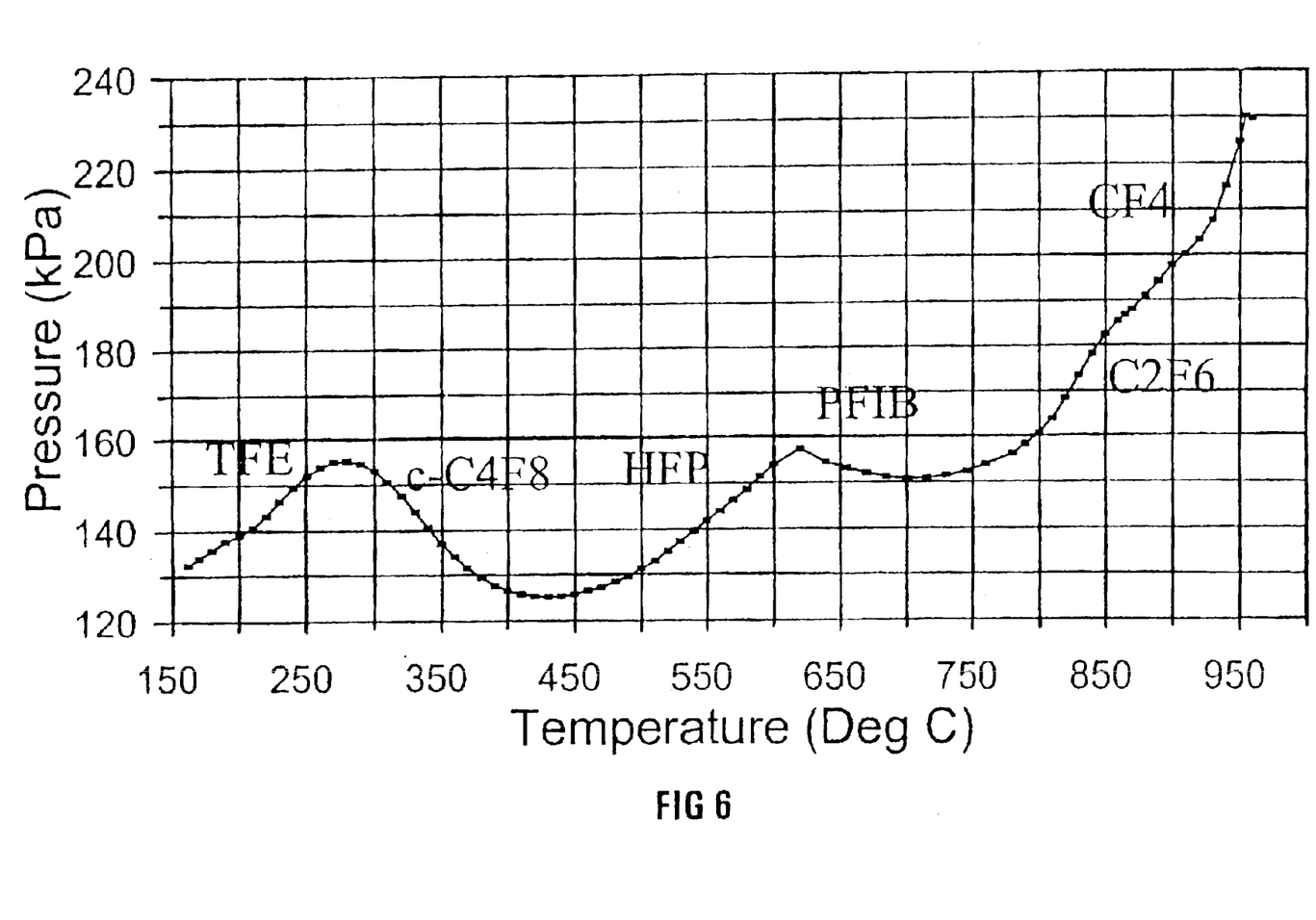
FIG. 6 shows, for TFE, a plot of reactor pressure against reactor temperature where the reactor has a fixed volume, for Example 2.

During preliminary test runs it was found that the reaction efficiency and the products formed are sensitive to both reactor pressure and crucible temperature. As a reference to guide the pressure dependency tests, another preliminary run was first performed. In this preliminary run, a closed container of a fixed volume having temperature and pressure measurement probes inside was utilized to heat incrementally a fixed amount of TFE through a temperature gradient while recording the gas pressure as a function of temperature. FIG. 6 was derived from this information. FIG. 6 shows a series of humps superimposed on a gradually increasing background of an ordinary P/T at constant volume curve. This shows the formation of different products at different temperatures with the corresponding pressure changes as the volume (number of molecules) changes. During a recombination reaction the pressure drops and during a dissociation reaction the pressure rises. Careful examination of the pressure slopes in conjunction with available reaction information enabled the identification of the dominant product for each temperature region. These are also indicated in FIG. 6. TFE for example starts to recombine to form c-$C_4F_8$ at a temperature of 270° C. In turn c-$C_4F_8$ starts to dissociate at a temperature of 450° C. and forms HFP. These products are stable when quenched. Since the production of HFP was the predominant goal in the subsequent test runs, the crucible temperatures were accordingly chosen in the vicinity of 600° C.

For these subsequent test runs, the installation 10 of FIGS. 1 and 2 was again operated on a continuous basis while FEP was fed continuously into the crucible (ID=54 mm, OD=64 mm, length=180 mm) where it was melted and chemically cracked. The coil around the crucible was modified to heat the crucible non-uniformly to create a temperature profile which increased from bottom to top. This was done, firstly, to prevent condensation of liquid or solid product before the quench probe was reached. Secondly, since the depolymerization reaction substantially takes place at the bottom of the crucible (lower temperature end), the upper end of the crucible must be hotter to ensure complete sublimation of the vapor. Thirdly the hot zone serves as a preheating zone for the FEP particles as they are fed into the crucible. During the first run the crucible was operated between 630° C. and 830° C. with the center at 710° C., the run being designated as "630° C.". The second run was operated between 600° C. and 780° C. with the center at 700° C., and accordingly designated "600° C.". The results are given in Table 2.

TABLE 2

| Pressure | 20 | 30 | 50 | 60 | 80 | 100 | 120 |
|---|---|---|---|---|---|---|---|
| 630° C. | | | | | | | |
| TFE | | 52 | | 30 | | 25 | 17 |
| HFP | | 38 | | 50 | | 52 | 64 |
| c$C_4F_8$ | | 10 | | 17 | | 18 | 14 |
| 600° C. | | | | | | | |
| TFE | 62 | | 47 | | 33 | 25 | 23 |
| HFP | 32 | | 37 | | 41 | 42 | 44 |
| c$C_4F_8$ | 5.4 | | 17 | | 27 | 28 | 28 |

TABLE 3

| | |
|---|---|
| Energy In (kW) | 4 |
| Enthalpy (kWh/kg) | 1.6 |
| Mass Flow FEP (kg/h) | 2.4 |
| Run duration (h) | 4 |
| $C_2F_4$ (kg/h) | 1.04 |
| $C_3F_6$ (kg/h) | 0.782 |
| c-$C_4F_8$ (kg/h) | 0.31 |
| Fluorine balance | 100% |
| Total Mass Balance | 89% |

Figure 7:
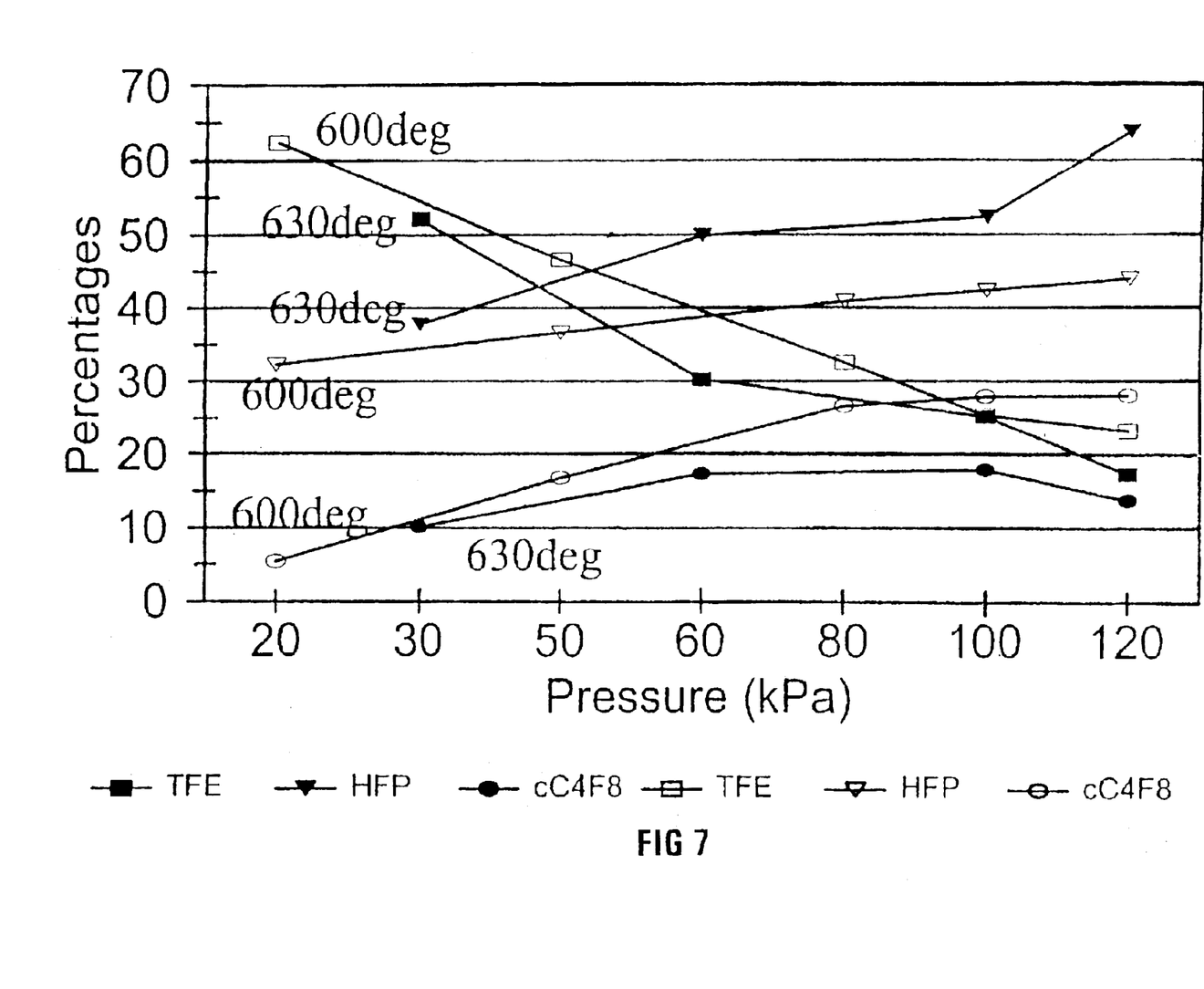
FIG. 7 shows, for FEP feedstocks, a plot of product yields against reactor pressure, for Example 2.
Figure 8:
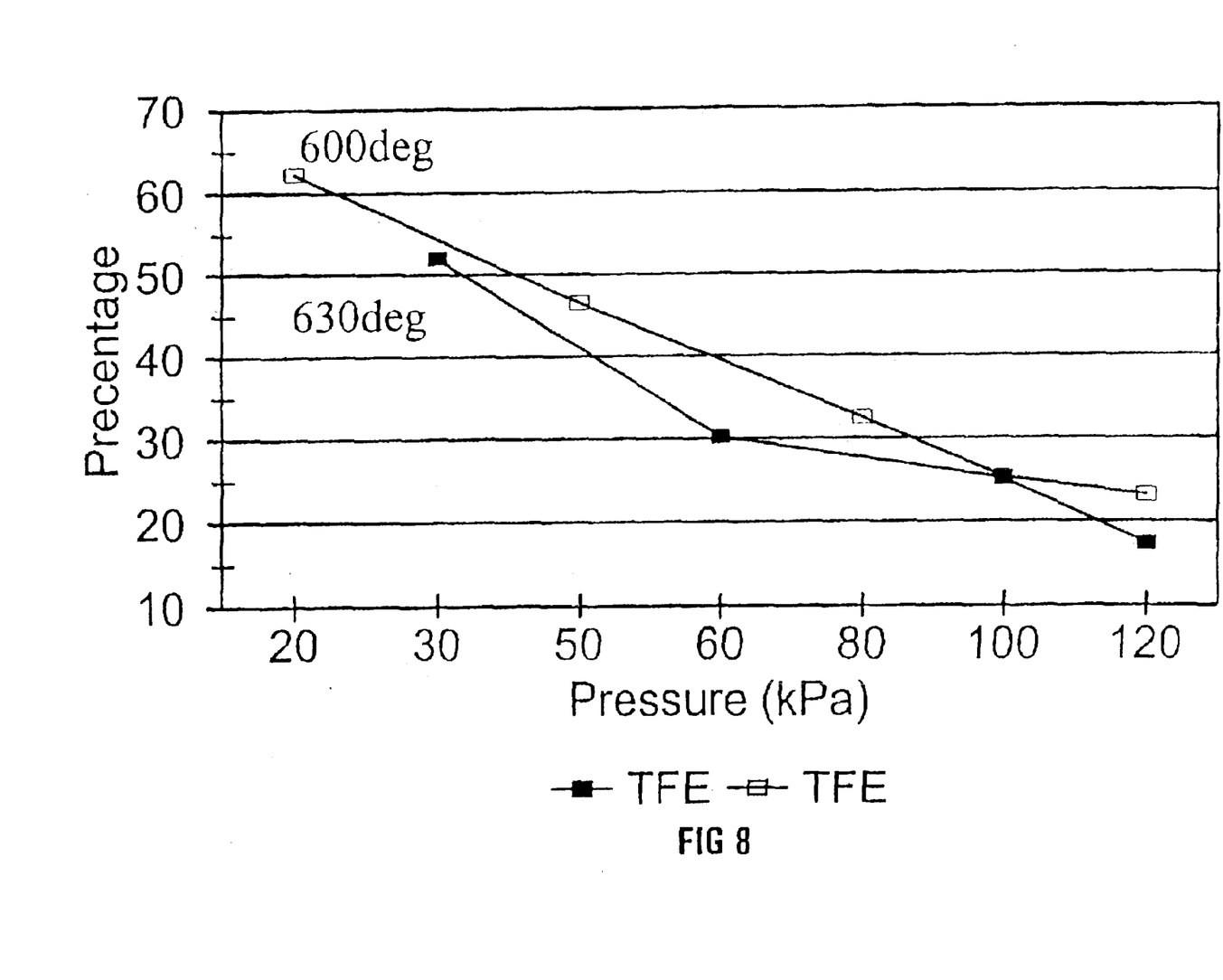
FIGS. 8 to 10 show excerpts from FIG. 7, for each of the products shown in FIG. 7.
Figure 9:
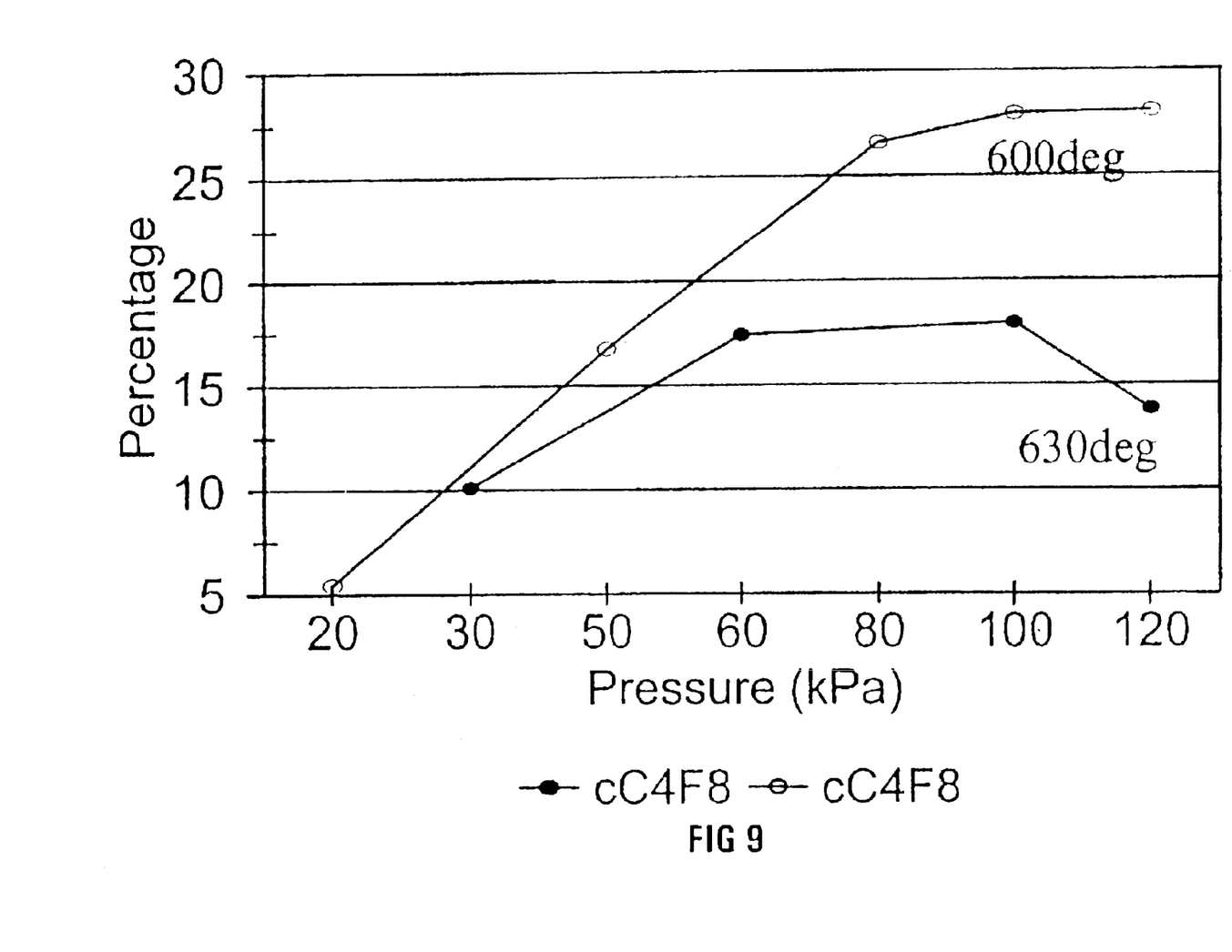
Figure 10:
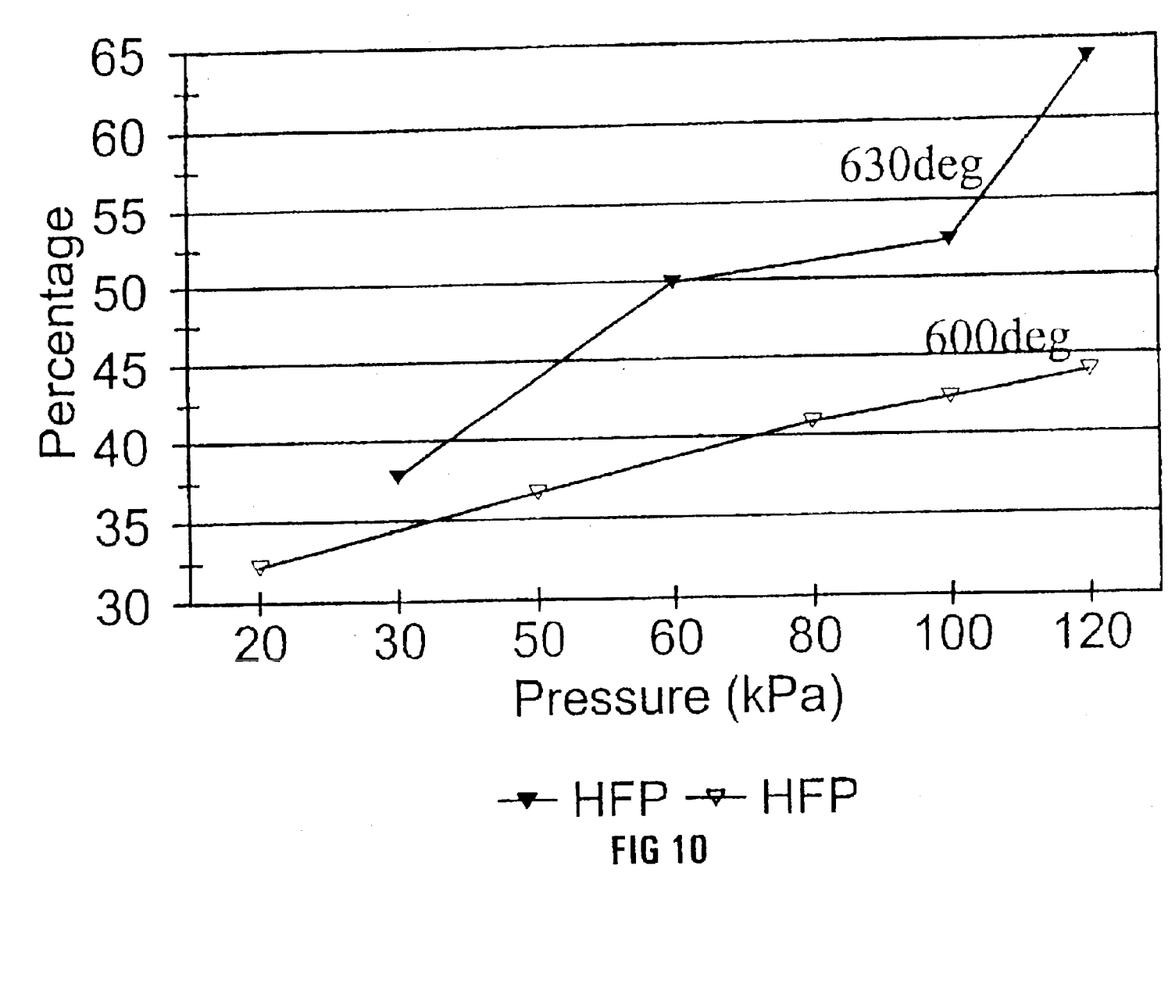

The results of Table 2 are represented graphically in FIG. 7 from which the pressure and temperature dependence of the product yield is evident. FIGS. 8–10 represent excerpts from FIG. 7, one for each of the products. Table 3 sets out the operating conditions, fluorine balance and a total mass balance. In respect of the total mass balance of 89%, the 11% mass loss is mainly due to solids forming on the cold surfaces.

Generally, FIG. 7 shows that as the pressure increases the yield of TFE decreases (see also FIG. 8), c-$C_4F_8$ moves through a maximum (see also FIG. 9) and HFP increases (see also FIG. 10). The latter two show a marked temperature effect in the sense that the higher crucible temperature profile yielded significantly more HFP and less c-$C_4F_8$. It is believed that the product gas retention time at the higher crucible temperature is long enough to form more HFP by decomposition of c-$C_4F_8$. In contrast, a much milder temperature effect is observed for TFE production (FIG. 8). This is probably due to the fact that in both runs the TFE production at the respective temperatures in the crucible has been completed (see FIG. 6) by the time the gas reaches the quench probe and what is observed here is its dissociation rate into the two successive products, the selectivity of which depends on the crucible temperature.

From the foregoing it is obvious that by further standard experimentation temperature and pressure parameter sets may be generated to optimally control the selectivity of at least the majority of desired product combinations. It is also obvious that the process could be extended to include the conversion of liquid not-directly usable fluorocarbon feed stocks.

This method of converting FEP into useful products proved to be inexpensive, safe, environmentally clean, versatile and easy to operate. Combined with a well developed distillation plant high purity, high quality and high value products can be produced.

Typical products that can be obtained with the method of the present invention are $C_xF_y$ chains, where x and y are integers. In such chains, when directed to TFE production, the main product is approximately 90% TFE.

It was found that the induction generator 12 is very efficient with little energy being lost to surroundings. The installation 10 has a very short start-up time.

Advantages of the method of the present invention are that no carrier gas is required, and that the product obtained is relatively pure. Thus, only a relatively simple distillation stage is normally required for separating the resultant TFE from the other products obtained.

By the method of the present invention, filled and unfilled not directly usable fluorocarbon materials can be depolymerized and transformed into relatively pure, high value products by means of pyrolysis, with a minimal downstream distillation requirement.

What is claimed is:

1. A method of treating a fluorocarbon feedstock, which method includes heating, by means of radio frequency induction, a heating zone of a reaction chamber to a temperature not exceeding 950EC;

allowing a fluorocarbon feedstock, comprising at least one fluorocarbon compound, to heat up in the heating zone;

choosing a reaction chamber pressure and a heating zone temperature so that the fluorocarbon compound dissociates or depolymerizes into at least one more desired fluorocarbon compound;

forming a hot product gas comprising the more desired fluorocarbon compound; and quenching the hot product gas to stabilize the more desired fluorocarbon compound.

2. A method according to claim 1, wherein the reaction chamber is provided by a reactor comprising an elongate cylindrical reactor shell, with the reaction chamber containing the heating zone, and with a feedstock holder being provided in the heating zone of the reaction chamber.

3. A method according to claim 2, wherein the radio frequency induction heating is provided by a radio frequency induction heating oven having an induction coil within which the heating zone of the reactor is located.

4. A method according to claim 2, wherein the reactor shell extends vertically and is stationary.

5. A method according to claim 2, wherein the reactor shell is tilted at an angle to the vertical and rotates or vibrates.

6. A method according to claim 5, wherein the reactor is provided with a graphite crucible having transverse baffles to regulate the residence time of the feedstock in the reactor.

7. A method according to claim 2, wherein the fluorocarbon feedstock is in liquid form, is a pure feedstock comprising a single fluorocarbon compound or is a not directly usable fluorocarbon product comprising two or more fluorocarbon compounds, with one compound being present in the product as a dominant component so that it constitutes a major proportion of the product, and is fed into the reactor from the bottom.

8. A method according to claim 2, wherein the fluorocarbon feedstock is in solid particulate form, is a filled or an unfilled not directly usable material, which has optionally been pretreated to remove surface contaminants, and is fed into the reactor from the top or the bottom.

9. A method according to claim 8, wherein the fluorocarbon feedstock is introduced into the reaction chamber by feeding it vertically and under gravity into the reaction chamber, immediately above the heating zone and wherein the feedstock particles are in the size range 1–10 mm.

10. A method according to claim 2, wherein the quenching of the hot product gas is effected in a second zone of the reaction chamber located above the heating or first zone thereof.

11. A method according to claim 10, wherein the quenching is effected by means of a self-cleaning quench probe.

12. A method according to claim 11, wherein the self-cleaning quench probe comprises an outer cylindrical component mounted to the reactor, providing a central passageway and adapted to cool the hot gas passing through the passageway; a plurality of circumferentially spaced elongate teeth or scrapers protruding inwardly from the outer component into the passageway; an inner cylindrical component located with clearance inside the outer component, with the inner component also adapted to cool the hot gas passing along the peripheral gap between the components; a plurality of circumferentially spaced elongate teeth or scrapers protruding outwardly from the inner component into the passageway, with these teeth or scrapers being staggered with respect to the teeth or scrapers on the outer component; and drive means for driving the one component to oscillate relative to the other component.

* * * * *